United States Patent [19]

Kuehnhanss

[11] 4,268,449
[45] May 19, 1981

[54] METHOD FOR THE PREPARATION OF FURAN-2-CARBOXYLIC ACID AMIDE AND THE CORRESPONDING FURAN-2-CARBOXYLIC ACID

[75] Inventor: Gerhard O. Kuehnhanss, Baton Rouge, La.

[73] Assignee: Ethyl Corporation, Richmond, Va.

[21] Appl. No.: 123,809

[22] Filed: Feb. 22, 1980

[51] Int. Cl.³ .......................................... C07D 307/54
[52] U.S. Cl. .................................................. 260/347.3
[58] Field of Search ...................................... 260/347.3

[56] References Cited

PUBLICATIONS

Zabicky, The Chemistry of Amides, Interscience Publishers, New York (1970), pp. 149, 150, 816–817.

Primary Examiner—Richard Raymond
Attorney, Agent, or Firm—Donald L. Johnson; John F. Sieberth

[57] ABSTRACT

Furan-2-carboxylic acid-amide and the corresponding furan-2-carboxylic acid are prepared by contacting carbamoyl chloride and furan at a temperature in the range of from about 10° to about 30° C. in a suitable reaction medium.

8 Claims, No Drawings

METHOD FOR THE PREPARATION OF FURAN-2-CARBOXYLIC ACID AMIDE AND THE CORRESPONDING FURAN-2-CARBOXYLIC ACID

This invention relates to the preparation of furan-2-carboxylic acid-amide and the corresponding furan-2carboxylic acid.

THE INVENTION

This invention involves the discovery that furan-2-carboxylic acid-amide and the corresponding acid can be formed in good yield and high purity by the simple expedient of contacting carbamoyl chloride and furan at a temperature in the range of from about 10° to about 30° in a suitable reaction medium to form the 2-acid-amide which can then be hydrolyzed to the acid. This reaction is accomplished without the necessity of a catalyst and furthermore only 2-substituted products are formed.

The process of this invention may be generally depicted by the following equation:

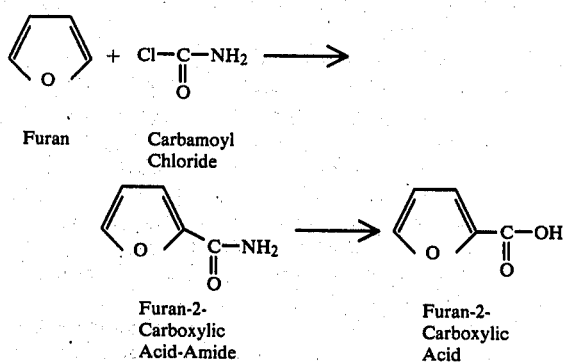

In the process furan-2-carboxylic acid-amide can be isolated from the reaction mixture and then hydrolyzed to the corresponding acid in a separate container; preferably the acid-amide is converted directly to the acid in the same vessel without the necessity of isolating the acid-amide. This can be accomplished by the addition of base to the medium in order to hydrolyze the amide to the acid.

In practicing this invention, contacting the furan and carbamoyl chloride should be effected within a temperature range so that the carbamoyl chloride is not substantially degraded. Preferably the furan and carbamoyl chloride are contacted at temperatures in the range of from about 10° to about 30° C. and most preferably between 15° and 25° C.

Suitable reaction media are those which facilitate the contacting of the reactants without interfering with the desired reaction. Accordingly, in the process use is made of a liquid inert reaction medium or diluent. Among the suitable solvents which may be used are saturated, halogenated hydrocarbons such as carbon tetrachloride, chloroform, methylene chloride, 1,2-dichloroethane, and the like; saturated or aromatic ethers such as diethyl ether, dioxane, dimethoxyethane, anisole, diphenyl ether, and the like; saturated hydrocarbons such as n-pentane, n-hexane, n-octane, n-decane, cyclopentane, cyclohexane, and the like; nitro compounds such as nitrobenzene, nitromethane, and the like; acetonitrile; acetic anhydride; and chlorinated aromatics such as chlorobenzene, and the like. Naturally, use should be made of compounds which exist in the liquid state at the reaction temperature and afford sufficient solvency for the reactants at the desired temperature. Compounds which contain olefinic unsaturation, or other functionality reactive with carbamoyl chloride are not desirable. Preferred solvents are those which have normal boiling points between about 10° and about 60° C., as these facilitate workup procedures. Methylene chloride is a particularly preferred solvent for use in the process because of its low cost, availability and favorable boiling characteristics. The amount of the liquid reaction medium used is generally discretionary; preferably the amount of solvent falls within the range of 50 to 300 mole percent based on the number of moles of the furan being used. If desired, amounts of solvent above or below the preferred amounts can be successfully employed. It will be appreciated that the reaction system should be essentially anhydrous.

The ratio of carbamoyl chloride to furan used may vary widely, however, it is preferred that this ratio be at least stoichiometric and in a particularly preferred embodiment a 10 to 20 percent excess of carbamoyl chloride is used.

Contacting of furan with carbamoyl chloride to form the acid-amide generally involves reaction periods falling within the range of from about 6 to about 20 hours, with 10 to 14 hours being preferred. The termination of the amidization reaction may be determined by monitoring the amount of HCl given off or by other means known to the art. At termination, or at any point desired during the reaction, workup of the product is accomplished by decomposition of any unreacted carbamoyl chloride, removal of any unreacted furan and conversion of the acid-amide to the corresponding acid. Preferably this workup is carried out in the order recited although deviations from this workup order permit production of the acid. For example, it may be desirable to remove unreacted furan prior to decomposition of the carbamoyl chloride.

Decomposition of the carbamoyl chloride is preferably effected by addition of an excess amount of water (i.e., a 0.8 to 100 mole percent excess above the theoretical stoichiometric amount necessary on the basis that one mole of water is required to decompose one mole of carbamoyl chloride) having a temperature of below 10° C. and preferably below about 5° C. Decomposition of the carbamoyl chloride by water yields ammonium chloride and carbon dioxide. Unreacted furan can be removed by means known to the art such as application of a vacuum to the reaction vessel or by the introduction of steam into the unreaction medium. The acid-amide can then be converted to the corresponding acid salt by the addition of an excess of a base, i.e., about 10 to about 15 percent excess based on the amount of acid-amide formed. Preferably, an inorganic base such as sodium hydroxide, potassium hydroxide, ammonia and the like is employed, with sodium hydroxide being particularly preferred. The product furan-2-carboxylic acid can then be isolated by addition of an acid (preferably an inorganic acid such as HCl, H$_2$SO$_4$, SO$_2$ and the like) followed by extraction and separation by means known in the art. For example, an extraction solvent such as diethyl ether, chloroform, and the like is added to the mixture containing the acid, the phase containing the acid is then removed, e.g., by decantation and the product furan-2-carboxylic acid is isolated by distillation of the extraction solvent.

Another method of converting the acid-amide to the acid entails addition of an excess amount of water having a temperature below 10° C. to decompose any residual carbamoyl chloride followed by saponification or hydrolysis of the acid-amide to the acid salt. This is effected by addition of an excess of base (preferably an inorganic base, and most preferably sodium hydroxide) at temperatures up to about 120° C. (preferably between about 4 and 18 hours). Any unreacted furan and unhydrolyzed acid-amide is then extracted with an inert, liquid solvent (e.g., a lower aliphatic halogenated hydrocarbon such as chloroform) followed by acidification of the acid salt. As above, the acid salt is preferably converted to the corresponding acid by addition of an inorganic acid such as HCl, $H_2SO_4$, $SO_2$ and the like. The product furan-2-carboxylic acid is then easily re-extracted with an inert, liquid solvent such as chloroform, diethyl ether and the like. The furan-2-carboxylic acid is then isolated by means known in the art such as distillation.

Furans which may be used in the process of this invention include furan, nitrofuran or alkyl furans having the formula

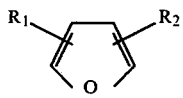

wherein $R_1$ and $R_2$ are, independently, hydrogen, nitro or alkyl each having up to about 3 carbon atoms with the proviso that at least one of the positions adjacent the oxygen atom carries a hydrogen substituent.

Carbamoyl chloride ($NH_2COCl$) is an unstable, colorless, pungent smelling liquid. It reacts explosively with water to give ammonium chloride and carbon dioxide and it decomposes visibly on standing. It can be stabilized by deep freezing and for a limited time (around 24 hours) by moderate cooling in solution with 1,2-dichloroethane or other solvents. L. Gattermann prepared this chloride for the first time in 1888 in a batch-wise manner by passing a stream of phosgene gas over heated aluminum chloride. Today, carbamoyl chloride is normally prepared continuously by reacting ammonia with phosgene in equal molar ratio at about 500° C. See Hopf, Ohlinger, and *Angew. Chem.*, 61 (5), 183 (1949).

A particular embodiment of the present invention is illustrated in the following example.

EXAMPLE

Carbamoyl chloride (7.94 grams, 0.1 moles) and furan (6.8 grams, 0.1 moles) in 10 ml (13.3 g, 0.16 moles) of methylene chloride were reacted for a period of about 12 hours at about 20° C. in a reaction vessel immersed in an ice-water bath. An excess of water having a temperature of about 3° C. was then added to the reaction mixture in order to decompose the unreacted carbamoyl chloride. After cessation of the vigorous decomposition reaction, steam was introduced into the reaction milieu for a period of 60 minutes in order to remove the unreacted furan. A 15 percent molar excess of sodium hydroxide (based on the amount of acid-amide produced) was then added to the reaction medium and this mixture was refluxed for 4 hours. After cooling, the reddish solution was freed from unhydrolyzed amide by extraction with chloroform followed by distillation of the chloroform to yield 1.7 grams of the amide. Subsequently, the amide-free solution was acidified using 20 percent hydrochloric acid. 3.3 Grams of furan-2-carboxylic acid were isolated by extraction with chloroform followed by water removal and distillation of the chloroform. The total yield of furan-2-carboxylic acid and furan-2-carboxylic acid-amide was 5 grams (0.0447 moles). Based on the total number of moles of furan used (0.1 moles), the yield was 44.7%.

The carboxylated furans disclosed herein are useful as intermediates for organic synthesis, especially in the preparation of oxygen containing drugs. For example, 5-nitrofuran is carboxylated to form 2-carboxylic acid-5-nitrofuran followed by reduction of the carboxyl group to an aldehyde functionality to form 5-nitrofurfural. Derivatives of this compound (e.g., nitrofuroxime) are known to possess both bacteriostatic and bactericidal properties. See Lednicer and Mitscher, *The Organic Chemistry of Drug Syntheses*, John Wiley and Sons, pp. 228–232 (1977).

What is claimed is:

1. A method for the preparation of furan-2-carboxylic acid-amide which comprises contacting carbamoyl chloride and furan without a catalyst at a temperature in the range of from about 10° C. to about 30° C. in an inert, liquid reaction medium.

2. A method of claim 1 wherein said contacting falls within the range of from about 6 to about 20 hours.

3. A method for the preparation of furan-2-carboxylic acid which comprises (i) contacting carbamoyl chloride and furan without a catalyst at a temperature in the range of from about 10° C. to about 30° C. in an inert, liquid reaction medium, and then (ii) adding excess base to the medium in order to form said acid.

4. A method for the preparation of furan-2-carboxylic acid which comprises
    (a) contacting carbamoyl chloride and furan without a catalyst at a temperature in the range of from about 10° C. to about 30° C. in an inert, liquid reaction medium, and then
    (b) adding an excess of water having a temperature of below about 10° C. to decompose the unreacted carbamoyl chloride, and then
    (c) introducing steam into said reaction medium to remove any unreacted furan therein, and then
    (d) adding an excess of base to said reaction medium to form said acid.

5. A method for the preparation of furan-2-carboxylic acid which comprises
    (a) contacting carbamoyl chloride and furan without a catalyst at a temperature in the range of from about 10° C. to about 30° C. in an inert, liquid reaction medium, and then
    (b) adding an excess of water having a temperature of below about 10° C. to decompose the unreacted carbamoyl chloride, and then
    (c) adding an excess of base at temperature of between about 30° C. and 120° C. for about 4 hours to about 18 hours, and then
    (d) extracting any unreacted furan and unhydrolyzed amide by the addition of an inert, liquid solvent, and then
    (e) acidifying the remaining mixture with an acid, and then
    (f) re-extracting the product furan-2-carboxylic acid with an inert, liquid solvent.

6. The method of claim 4 or 5 wherein said contacting is at a temperature of between about 15° and 25° C. and for a time period of from about 6 to about 20 hours.

7. The method of claim 4 or 5 wherein said furan-2-carboxylic acid is isolated from the reaction medium.

8. A method for the preparation of furan-2-carboxylic acid which comprises
   (a) contacting carbamoyl chloride and furan without a catalyst at a temperature between about 15° and 25° C. in the presence of an inert, low boiling, halogenated hydrocarbon reaction medium, and then
   (b) adding an excess of water having a temperature below about 5° C. to said reaction medium, and then
   (c) removing unreacted furan by the introduction of steam into the reaction medium, and then
   (d) adding from about 10 to about 15 percent excess of sodium hydroxide based on the amount of furan-2-acid-amide formed in order to hydrolyze said amide, and then
   (e) isolating furan-2-carboxylic acid.

* * * * *